(12) United States Patent
Holmström et al.

(10) Patent No.: US 8,060,201 B2
(45) Date of Patent: Nov. 15, 2011

(54) MEDICAL DEVICE

(75) Inventors: Nils Holmström, Järfälla (SE); Kjell Noren, Solna (SE)

(73) Assignee: St. Jude Medical AB, Jarfalla (SE)

( * ) Notice: Subject to any disclaimer, the term of this patent is extended or adjusted under 35 U.S.C. 154(b) by 584 days.

(21) Appl. No.: 12/095,241

(22) PCT Filed: Dec. 16, 2005

(86) PCT No.: PCT/SE2005/001956
§ 371 (c)(1),
(2), (4) Date: May 28, 2008

(87) PCT Pub. No.: WO2007/069962
PCT Pub. Date: Jun. 21, 2007

(65) Prior Publication Data
US 2008/0294214 A1 Nov. 27, 2008

(51) Int. Cl.
*A61N 1/00* (2006.01)
(52) U.S. Cl. .............................. 607/9; 607/27
(58) Field of Classification Search .................. 607/4–28
See application file for complete search history.

(56) References Cited

U.S. PATENT DOCUMENTS

| | | | |
|---|---|---|---|
| 5,554,177 A | 9/1996 | Kieval et al. | |
| 5,700,283 A | 12/1997 | Sato | |
| 5,836,987 A | 11/1998 | Baumann et al. | |
| 6,044,298 A | 3/2000 | Sato et al. | |
| 6,058,329 A * | 5/2000 | Salo et al. | 607/17 |
| 6,643,548 B1 | 11/2003 | Mai et al. | |
| 6,650,940 B1 | 11/2003 | Zhu et al. | |
| 2002/0151938 A1 | 10/2002 | Corbucci | |
| 2004/0127792 A1 | 7/2004 | Siejko et al. | |
| 2005/0149136 A1 | 7/2005 | Siejko et al. | |
| 2006/0161070 A1* | 7/2006 | Siejko et al. | 600/528 |

FOREIGN PATENT DOCUMENTS

| | | |
|---|---|---|
| WO | WO 95/27531 | 10/1995 |
| WO | WO 01/56651 | 8/2001 |

* cited by examiner

*Primary Examiner* — Scott Getzow
(74) *Attorney, Agent, or Firm* — Schiff Hardin LLP

(57) ABSTRACT

A method for operating an implantable medical device to control a stimulation therapy includes the steps of: sensing an acoustic energy; producing acoustic signals indicative of heart sounds of the heart of the patient over predetermined periods of a cardiac cycle during successive cardiac cycles; extracting a signal corresponding to a first heart sound (S1) from a measured acoustic signal; calculating an energy value corresponding to the extracted signal; storing the energy value corresponding to the first heart sound; and initiating an optimization procedure, the optimization procedure comprising the steps of: iteratively controlling a delivery of the pacing pulses based on successive energy values corresponding to successive first heart sound signals and determining an optimal PV interval or AV interval with respect to the energy values. A medical device and a computer readable medium to implement the method.

22 Claims, 8 Drawing Sheets

MEDICAL DEVICE

This application is a National Stage entry of PCT/SE2005/001956, filed Dec. 16, 2005.

BACKGROUND OF THE INVENTION

1. Field of the Invention

The present invention generally relates to implantable medical devices, such as cardiac pacemakers and implantable cardioverter/defibrillators, and in particular to a method, a medical device, a computer program product and a computer readable medium for controlling a stimulation therapy using detected heart sounds.

2. Description of the Prior Art

Auscultation is an important diagnostic method for obtaining information of the heart sounds, which is well established as diagnostic information of the cardiac function. The sounds are often described as S1-S4. During the working cycle of the heart mechanical vibrations are produced in the heart muscle and the major blood vessels. Acceleration and retardation of tissue cause the vibrations when kinetic energy is transformed to sound energy, e.g. at valve closing. Vibrations can also arise from turbulent blood flow, e.g. at stenosis and regurgitation. These vibrations may be listened to using a stethoscope or registered electronically using phonocardiography, i.e. graphical registration of the heart sounds by means of a heart microphone placed on the skin of the patient's thorax. Auscultation using a stethoscope is, to a large extent, built on practical experience and long practice since the technique is based on the doctor's interpretations of the hearing impressions of heart sounds. When applying phonocardiography, as mentioned above, a heart microphone is placed on the skin of the patient's thorax. In other words, it may be cumbersome and time-consuming to obtain knowledge of the heart sounds and the mechanical energy during the heart cycle using these manual or partly manual methods and, in addition, the obtained knowledge of the heart sounds may be inexact due to the fact that the knowledge is, at least to some extent, subjective.

The first tone S1 coincides with closure of the Mitral and Tricuspid valves at the beginning of systole. Under certain circumstances, the first tone S1 can be split into two components. An abnormally loud S1 may be found in conditions associated with increased cardiac output (e.g. fever, exercise, hyperthyroidism, and anemia), tachycardia and left ventricular hypertrophy. A loud S1 is also characteristically heard with mitral stenosis and when the P-R interval of the EKG is short. An abnormally soft S1 may be heard with mitral regurgitation, heart failure and first degree A-V block (prolonged P-R interval). A broad or split S1 is frequently heard along the left lower sternal border. It is a rather normal finding, but a prominent widely split S1 may be associated with right bundle branch block (RBBB). Beat-to-beat variation in the loudness of S1 may occur in atrial fibrillation and third degree A-V block.

The second heart sound S2 coincides with closure of the aortic and pulmonary valves at the end of systole. S2 is normally split into two components (aortic and pulmonary valves at the end of systole) during inspiration. Splitting of S2 in expiration is abnormal. An abnormally loud S2 is commonly associated with systemic and pulmonary hypertension. A soft S2 may be heard in the later stages of aortic or pulmonary stenosis. Reversed S2 splitting (S2 split in expiration—single sound in inspiration) may be heard in some cases of aortic stenosis but is also common in left bundle branch block (LBBB). Wide (persistent) S2 splitting (S2 split during both inspiration and expiration) is associated with right bundle branch block, pulmonary stenosis, pulmonary hypertension, or atrial septal defect.

The third heart sound S3 coincides with rapid ventricular filling in early diastole. The third heart sound S3 may be found normally in children and adolescents. It is considered abnormal over the age of 40 and is associated with conditions in which the ventricular contractile function is depressed (e.g. CHF and cardiomyopathy). It also occurs in those conditions associated with volume overloading and dilation of the ventricles during diastole (e.g. mitral/tricuspid regurgitation or ventricular septal defect). S3 may be heard in the absence of heart disease in conditions associated with increased cardiac output (e.g. fever, anemia, and hyperthyroidism).

The fourth heart sound S4 coincides with atrial contraction in late diastole. S4 is associated with conditions where the ventricles have lost their compliance and have become "stiff". S4 may be heard during acute myocardial infarction. It is commonly heard in conditions associated with hypertrophy of the ventricles (e.g. systemic or pulmonary hypertension, aortic or pulmonary stenosis, and some cases of cardiomyopathy). The fourth heart sound S4 may also be heard in patients suffering from CHF.

Thus, the systolic and diastolic heart functions are reflected in the heart sound. The power of energy value of the heart sounds and their relation may carry information of the workload and status of the heart. For example, as discussed above, patients with a wide QRS complex due to e.g. right bundle branch block (RBBB) or A-V block are associated with a widened or split first heart sound S1. Furthermore, changes of the energy of e.g. S1 over time can be a useful tool, for example, in diagnosis of different conditions. A high variability of the energy parameters during otherwise constant conditions indicates, for example, that filling is altering due to e.g. arrhythmia or conduction disorder. As can be understood from the above-mentioned, knowledge of the heart sounds and the corresponding mechanical energy can be used for diagnosis/monitoring and controlling pacing therapy of patients. In addition, this knowledge can also be used to optimize a stimulation therapy and to verify that the stimulation output evokes a desired response in a selected region of the heart. In patients suffering from heart failure, such as Congestive Heart Failure (CHF), the knowledge of the heart sounds and the corresponding energy parameters can be used to estimate the severity of the condition and/or to optimize the AV delay. Consequently, it would be beneficial if signals related to the heart sounds and the corresponding energy could be collected and used for controlling/optimizing pacing therapy in an automated manner.

The known technique presents a number of automated systems for controlling/optimizing stimulation therapy. For example, medical devices and methods in such devices for optimizing AV delay are known. In U.S. Pat. No. 5,700,283, a method and apparatus for pacing patients with severe congestive heart failure is shown. The heart sounds are sensed and used to derive a mechanical AV delay of the patient's heart. The pacemaker applied AV delay is adjusted until the measured AV falls in a predetermined range of between 180 ms to 250 ms. This solution may require extensive signal processing in order to derive the mechanical AV delay of the heart from the sensed heart sounds. In U.S. Pat. No. 6,044,298, a method and apparatus for optimizing a pacing mode of a cardiac pacemaker for patients having CHF are shown. The Total Acoustic Noise (TAN) is measured and an optimum pacing mode is determined by detecting the particular mode associated with the minimum TAN, wherein the integrated value of the acoustic signal during a single heart beat cycle (from P-wave to P-wave or from R-wave to R-wave) is referred to as the total acoustic noise (TAN). However, the total acoustic noise is blunt tool in the optimization of the AV interval due to the fact that it comprises noise from of a large number of sources including, for example, the first heart sound to the fourth heart sound (S1-S4). In addition, other factors such as activity level of the patient, position of the patient, etc. also affect and/or contribute to the noise. This may, for example, introduce errors since it may be difficult to identify which noise source that contributes to the total noise signal and to what extent different sources contribute to it, which, in turn, may entail unreliable optimization results. Hence, the optimization may be based, at least in part, on erroneous information. In WO 01/56651 a system and method for adjusting AV delay by monitoring heart sounds S1 and S2 is disclosed. The presence or absence of one or more of the heart sounds S1 and S2 in the sensor signal indicates whether a stimulation pulse evokes the desired response in the patient's heart. This solution is thus directed to monitoring whether a desired response was obtained where the presence of a predetermined heart sound indicates capture rather than optimizing the AV delay.

Thus, there is a need of a method and a medical device that are capable of automatically controlling the stimulation therapy, and in particular the AV or PV delay, and that provide reliable optimization results using detected heart sounds.

SUMMARY OF THE INVENTION

Thus, an object of the present invention is to provide a method and medical device that are capable of automatically controlling the stimulation therapy, in particular the AV or PV delay.

Another object of the invention is to provide reliable and accurate optimization results using detected heart sounds.

According to an aspect of the present invention, there is provided an implantable medical device including a pulse generator adapted to produce cardiac stimulating pacing pulses, the device being connectable to at least one lead comprising electrodes for delivering the pulses to cardiac tissue in at least one atrium and/or in at least one ventricle of a heart of a patient. The device has a signal processing circuit adapted to extract a signal corresponding to a first heart sound (S1) from a measured acoustic signal, which signal has been received from an acoustic sensor adapted to sense an acoustic energy and to produce acoustic signals indicative of heart sounds of the heart of the patient over predetermined periods of a cardiac cycle during successive cardiac cycles, and to calculate an energy value corresponding to the extracted signal; a storage unit that stores the energy value corresponding to the first heart sound and/or the extracted signal; and a controller adapted to initiate an optimization procedure, wherein a delivery of the pacing pulses is controlled iteratively based on successive energy values corresponding to successive first heart sound signals to determine an optimal PV interval or AV interval with respect to the energy values.

According to a second aspect of the present invention, there is provided method for operating an implantable medical device to control a stimulation therapy, which device includes a pulse generator adapted to produce cardiac stimulating pacing pulses and which device is connectable to at least one lead comprising electrodes for delivering the pulses to cardiac tissue in at least one atrium and/or in at least one ventricle of a heart of a patient. The method includes the steps of sensing an acoustic energy; producing acoustic signals indicative of heart sounds of the heart of the patient over predetermined periods of a cardiac cycle during successive cardiac cycles; extracting a signal corresponding to a first heart sound (S1) from a measured acoustic signal; calculating an energy value corresponding to the extracted signal; storing the energy value corresponding to the first heart sound; and initiating an optimization procedure, the optimization procedure comprising the steps of: iteratively controlling a delivery of the pacing pulses based on successive energy values corresponding to successive first heart sound signals and determining an optimal PV interval or AV interval with respect to the energy values.

According to a further aspect of the present invention, there is provided a computer readable medium encoded with programming instructions that cause a computer to perform a method according to the second aspect of the present invention.

Thus, the invention is based on the insight that the amplitude of the E1 signal, i.e. the energy value corresponding to the first heart sound (S1), is closely related to the length of the AV or PV interval. In particular, the E1 signal depends highly on the AV or PV interval in that a too short AV interval gives an abnormally high E1 value while a long AV interval gives a low E1 value. Moreover, a certain amplitude of the E1 signal is associated with a specific activity level or activity level range at a normal cardiac function. That is, at a certain cardiac function there exists a suitable or optimal energy value or range for each activity level or activity level range. Thus, the optimization of the AV or PV interval according to the present invention is based on the above-mentioned findings in that a delivery of pacing pulses is iteratively controlled based on successive energy values corresponding to successive first heart sound signals and an optimal PV interval or AV interval is determined with respect to the energy values.

The present invention provides several advantages. For example, one advantage is that the optimization procedure for identifying an optimal AV or PV delay with respect to the energy value can be performed on a continuous and automated basis.

Another advantage is that the optimization can adapt to changing conditions of a heart of patient in a fast and reliable way since intrinsic information of the heart, i.e. the heart sounds, is used as input to the optimization procedure. The optimization is also accurate due to the facts that the systolic and diastolic heart functions are reflected in the heart sound, and that the heart sounds and their relations thus carry information of the workload and status of the heart.

The fact that the heart sounds are obtained by means of an implantable medical device connectable to an acoustic sensor that senses sounds or vibrations inside or outside the heart also contributes to higher degree of accuracy and reliability.

A further advantage of the present invention is that it is possible to study changes of the energy over time, which may provide useful information regarding, for example, the variability of the energy parameters. This information can, in turn, be used as an indicator of, for example, a changed filling due to e.g. arrhythmia or conduction disorder. Furthermore, the collected energy information can be used to estimate the severity of congestive heart failure and thus to optimize the AV delay with respect to this condition. In addition, the collected energy information may be used to tune a combination of drugs given to the patient.

According to an embodiment of the present invention, the PV interval or AV interval is gradually adjusted until the optimal PV interval or AV interval with respect to the energy values can be determined. The fact that the E1 signal depends highly on the AV or PV interval in that a too short AV interval gives an abnormally high E1 value while a long AV interval gives a low E1 value is used. The PV interval or AV interval may be gradually adjusted until a present energy level is within a predetermined energy value range. Thereby, a fast and reliable optimization procedure can be obtained.

In another embodiment of the present invention, the optimization procedure comprises the steps of, upon initiation of the optimization procedure, select a first PV or AV interval and gradually reduce the first PV interval or AV interval; compare an energy value corresponding to the first heart sound resulting from delivered pacing pulses in accordance with a latest PV or AV interval with an energy value corresponding to the first heart sound resulting from delivered pacing pulses in accordance with a preceding PV or AV interval and determine a PV or AV interval to be optimal when the comparison between successive energy values indicates an increase of energy level of the first heart sounds.

According to yet another embodiments of the present invention, a delivery of ventricular pacing pulses is controlled such that a VV interval is kept substantially constant during the optimization procedure and the PV or AV interval is determined to be optimal for the present VV interval.

In another embodiment of the present invention, an activity level of the patient is sensed and upon initiation of the optimization procedure, a first PV or AV interval is selected and the first PV interval or AV interval is gradually adjusted until an energy value corresponding to the first heart sound resulting from at least one delivered pacing pulse in accordance with a latest PV or AV interval is within a predetermined energy value range associated with the sensed activity level. The fact that, at a certain cardiac function, there exists a suitable or optimal energy value or energy value range for each activity level or activity level range is used. Thereby, a fast and reliable optimization procedure can be obtained. In addition, by performing this optimization procedure at two or more activity levels, it is possible to extrapolate the data to obtain a rate adaptive AV or PV delay.

According to an alternative embodiment, interventricular pacing timing parameters for at least one electrode is iteratively adjusted based on the energy values.

In yet another embodiment of the present invention, a bandpass filter is adapted to filter off frequency components of the acoustic signal outside a predetermined frequency range. The bandpass filter may have a frequency range of 10 to 300 Hz. The filtered signal is rectified to produce a signal containing only positive or zero values and at least one local maximum point being coincident with a first heart sound signal is identified in the rectified signal. To produce the energy value corresponding to the specific heart sound, the first heart sound signal is integrated in a predetermined time window comprising the at least one local maximum point. Alternatively, a squaring procedure is performed on the filtered signal to produce a signal containing only positive or zero values. A further alternative to the rectifying is to determine absolute values of the filtered signal. At least one local maximum point being coincident with a first heart sound signal is identified in the squared signal and the first heart sound signal is integrated in a predetermined time window comprising the at least one local maximum point to produce the energy value corresponding to the specific heart sound, wherein an energy value corresponding to the first heart sound can be obtained.

In a further embodiment of the present invention, a part of the signal containing only positive or zero values, i.e. the rectified or squared signal, above a predetermined threshold is selected and the part of the signal above the predetermined threshold is integrated, wherein an energy value corresponding to the first heart sound can be obtained.

In an embodiment of the present invention, each energy value is calculated as a mean value over a predetermined number of successive energy values. Thereby, more reliable and accurate energy values can be obtained. Alternatively, a weighted average value of a predetermined number of successive energy values can be used. In still another embodiment, a moving average of a predetermined number of successive energy values of heart sound signals is utilized.

In another embodiment of the present invention, an activity level of the patient is sensed and it is checked whether the sensed activity level is below a predetermined activity level. If it is determined the sensed activity level is below the predetermined activity level or activity level range, the optimization procedure is initiated. By performing the optimization at stable conditions, e.g. correlating the optimization procedure with a predetermined activity level, the accuracy and reliability of the procedure can be further enhanced. This predetermined activity level can, for example, be set such that the optimization is performed at rest. That is, in this case an AV or PV delay that is optimal for situations when the patient is at rest can be obtained.

According to yet another embodiment of the present invention, an activity level of the patient is sensed and it is checked whether the sensed activity level is below a predetermined first activity level (or within a first range) or within a second activity level range between a second activity level and a third activity level, wherein second activity level can be equal to or higher than the first activity level or equal to or higher than an upper limit of the first range. If the sensed activity level is found to be below the predetermined first activity level, an optimization procedure is initiated to identify a first AV or PV interval for the first activity level, and if the sensed activity level is found to be within the activity level range, an optimization procedure is initiated to identify a second AV interval or PV interval for the activity level range. Thus, the optimization can be performed at two activity levels, and the AV or PV interval can be optimized, for example, at rest and at an elevated activity level (e.g. at exercise), respectively. By knowing the optimal AV or PV delay at two activity levels, it is possible to extrapolate the data to obtain a rate adaptive AV or PV delay.

According to an alternative embodiment, a heart rate of the patient is sensed and it is determined whether the sensed heart rate is within a predetermined heart rate interval. If it is determined that the sensed heart rate is within the predetermined heart rate interval, an optimization procedure is initiated. By performing the optimization at stable conditions, e.g. correlating the optimization procedure with a predetermined heart rate level, the accuracy and reliability of the optimization procedure can be further improved.

According to another embodiment, at least one body position of the patient is detected and it is determined whether the patient is in at least one predetermined specific body position. If it is determined that the patient is in the predetermined position, an optimization procedure is initiated. By performing the optimization at stable conditions, e.g. correlating the optimization procedure with a predetermined position, the accuracy and reliability of the optimization procedure can be improved. Furthermore, the optimization can be performed at two different positions, for example, when the patient is in supine (lying down) and when the patient is in an upright position and thus an optimal AV or PV delay can be obtained for the supine position and an optimal AV or PV delay can be obtained for the upright position. In this way, the AV or PV delay can be optimized during different conditions.

In alternative embodiments, the optimization can be synchronized with anyone, some, or all of the following: heart rate, activity level, AV delay, pacing rate, or position of patient.

In embodiments, the acoustic sensor is arranged in a lead connectable to the device and is located e.g. in the right ventricle of the heart of the patient, in the left ventricle or in a coronary vein on the middle of the left ventricle. In addition, the sensor may be located in any suitable position in the body of a patient, e.g. vena cava, epicardially, or other places in thorax.

According to embodiments, the acoustic sensor is an accelerometer, a pressure sensor or a microphone.

In an alternative embodiment, the sensor is arranged within a housing of the implantable device.

As realized by the person skilled in the art, the methods of the present invention, as well as preferred embodiments thereof, are suitable to realize as a computer program or a computer readable medium.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

DESCRIPTION OF THE PREFERRED EMBODIMENTS

Figure 1:
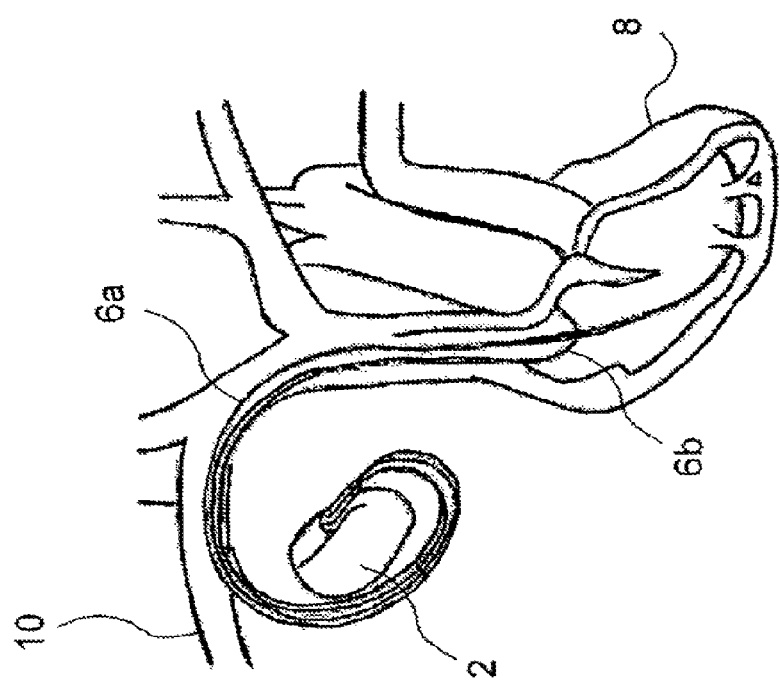
FIG. 1 is schematic diagram showing a medical device implanted in a patient in which device the present invention can be implemented.

With reference to FIG. 1, there is shown a schematic diagram of a medical device implanted in a patient in which device the present invention can be implemented. As seen, this embodiment of the present invention is shown in the context of a pacemaker 2 implanted in a patient (not shown). The pacemaker 2 comprises a housing being hermetically sealed and biologically inert. Normally, the housing is conductive and may, thus, serve as an electrode. The pacemaker 2 is connectable to one or more pacemaker leads, where only two are shown in FIG. 1 namely a ventricular lead 6a and an atrial lead 6b. The leads 6a and 6b can be electrically coupled to the pacemaker 2 in a conventional manner. The leads 6a, 6b extend into the heart 8 via a vein 10 of the patient. One or more conductive electrodes for receiving electrical cardiac signals and/or for delivering electrical pacing to the heart 8 are arranged near the distal ends of the leads 6a, 6b. As will be apparent to those skilled in the art, the leads 6a, 6b may, for example, be implanted with their distal ends located in either the right atrium or right ventricle of the heart 8. Moreover, they may be in form of epicardial leads attached directly at the epicardium, they may be located in the left ventricle or in a coronary vein on the middle of the left ventricle. In addition, leads comprising a sensor may be located in any suitable position in the body of a patient, e.g. vena cava, or other places in thorax.

Figure 2:
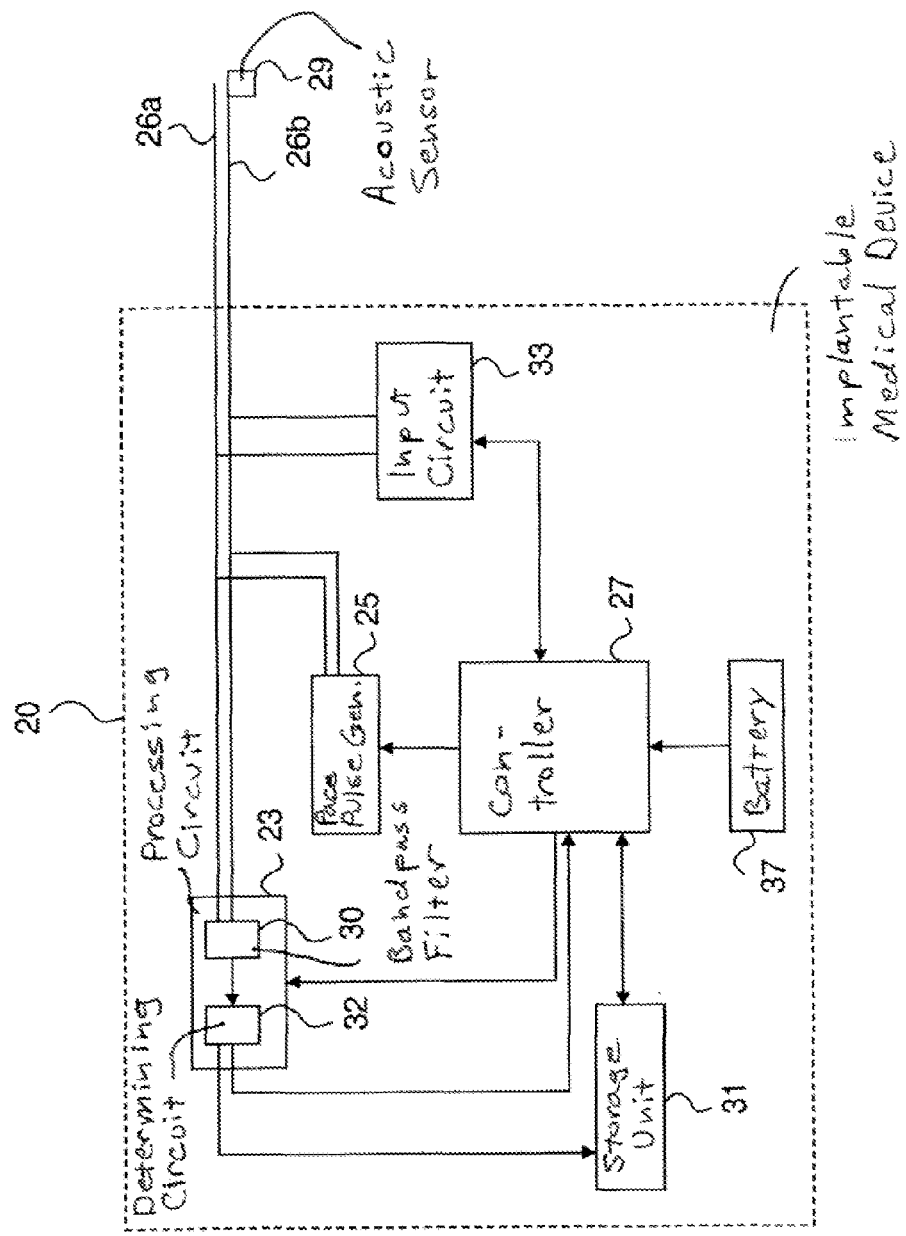
FIG. 2 is block diagram of the primary functional components of a first embodiment of the medical device according to the present invention.

With reference now to FIG. 2, the configuration including the primary components of an embodiment of the present invention will be described. The illustrated embodiment comprises an implantable medical device 20, such as the pacemaker shown in FIG. 1. Leads 26a and 26b, of the same type as the leads 6a and 6b shown in FIG. 1, are connectable to the device 20. The leads 26a, 26b may be unipolar or bipolar, and may include any of the passive or active fixation means known in the art for fixation of the lead to the cardiac tissue. As an example, the lead distal tip (not shown) may include a tined tip or a fixation helix. The leads 26a, 26b carry one or more electrodes (as described with reference to FIG. 1), such as a tip electrode or a ring electrode, arranged to, inter alia, measure the impedance or transmit pacing pulses for causing depolarization of cardiac tissue adjacent to the electrode (-s) generated by a pace pulse generator 25 under influence of a controller 27 including a microprocessor. The controller 27 controls, inter alia, pace pulse parameters such as output voltage and pulse duration.

Furthermore, an acoustic sensor 29 is arranged in or connected to one of the leads 26a, 26b. Alternatively, the acoustic sensor is located within the housing of the device 20. In one embodiment, the acoustic sensor 29 is arranged in a lead located in a right ventricle of the heart, in coronary sinus or the great cardiac vein of the patient. The acoustic sensor 29 may, for example, be an accelerometer, a pressure sensor, or a microphone. The acoustic sensor 29 is adapted to sense acoustic energy of the heart and to produce signals indicative of heart sounds of the heart of the patient. For example, the acoustic sensor 29 may sense the acoustic energy over predetermined periods of a cardiac cycle during successive cardiac cycles. In one embodiment of the present invention, a sensing session to obtain a signal indicative of a first heart sound (S1) is synchronized with a detected heart event, e.g. detection of an intrinsic or paced QRS-complex.

Furthermore, the implantable medical device 20 comprises a signal processing circuit 23 adapted to process the sensed signal to extract a signal corresponding to a first heart sound (S1) and to calculate an energy value corresponding to the extracted signal. In one embodiment, the signal processing circuit 23 includes pre-process circuits including at least one bandpass filter 30 adapted to filter off frequency components of the heart sound signal outside a predetermined frequency range, for example, 10-300 Hz, and a determining circuit 32 adapted to determine the absolute value of the bandpass filtered signal and to produce a resulting absolute value heart sound signal. The bandpass filter 30 is, for example, a digital filter of second order and the filtering process is performed as a zero-phase procedure to cancel out time delays introduced by the filter, and hence the signal is filtered twice, first in a forward direction and in then in a backward direction. As alternatives to the determining means, a rectifier can be used to rectify the filtered signal or the filtered signal can be squared to obtain the instantaneous power of the filtered signal. The signal processing circuit 23 also has an energy calculating circuit 34 adapted to calculate an energy value corresponding to the filtered signal. For example, the energy calculating circuit 34 may include an identifying circuit 36 adapted to identify at least one local maximum point being coincident with a first heart sound (S1) and an integrator 38 adapted to integrate the filtered signal over a predetermined time window exhibiting the local maximum point, wherein an energy value of the filtered signal is obtained.

A storage unit 31 is connected to the controller 27, which storage means 31 may include a random access memory (RAM) and/or a non-volatile memory such as a read-only memory (ROM). Detected signals from the patients heart are processed in an input circuit 33 and are forwarded to the controller 27 for use in logic timing determination in known manner. The implantable medical device 20 is powered by a battery 37, which supplies electrical power to all electrical active components of the medical device 20. Data contained in the storage means 31 can be transferred to a programmer (not shown) via a programmer interface (not shown) for use in analyzing system conditions, patient information, etc.

Figure 3:
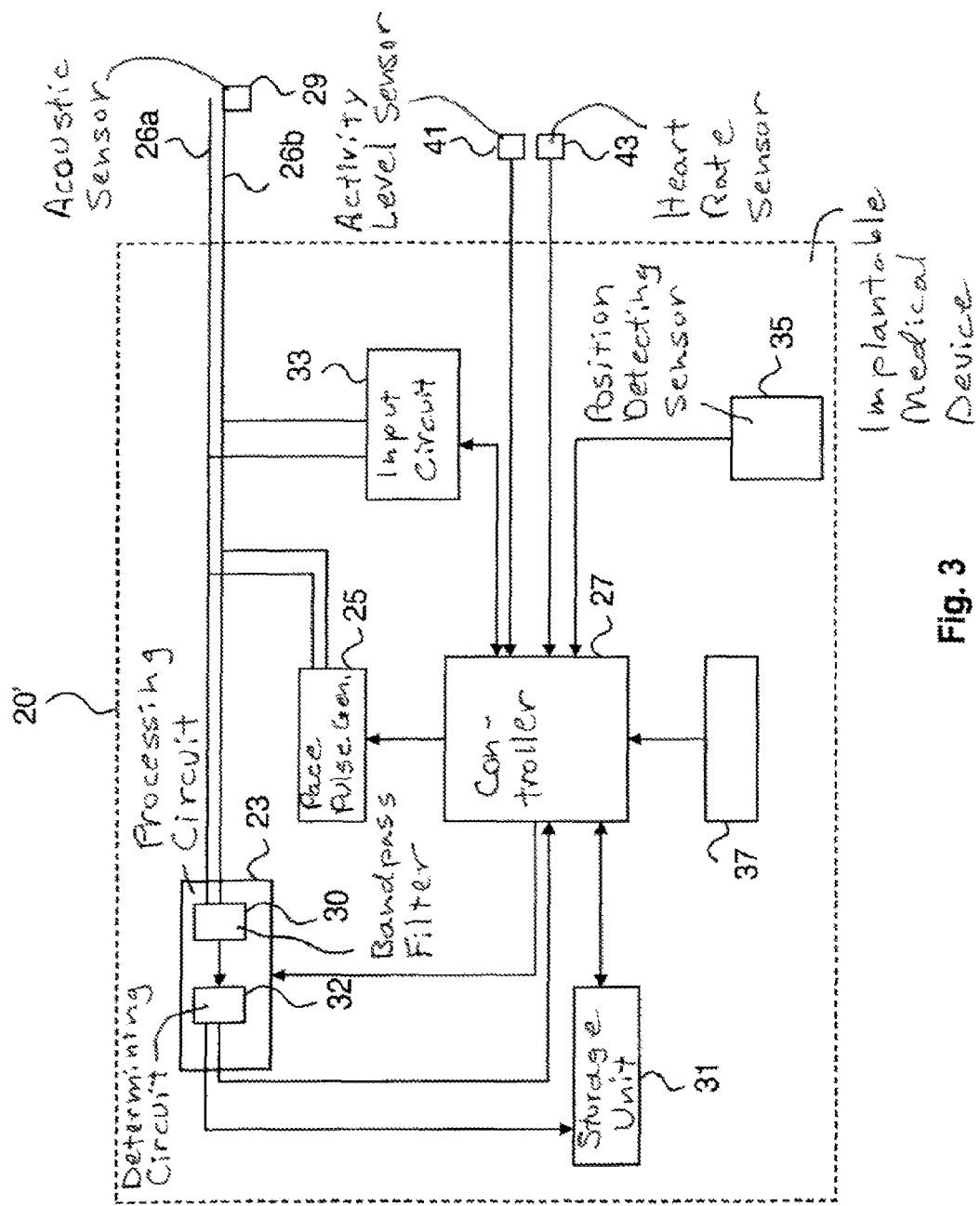
FIG. 3 is a block diagram of the primary functional components of another embodiment of the medical device according to the present invention.

With reference now to FIG. 3, another embodiment of the present invention will be described. Like parts in FIG. 2 and FIG. 3 are denote with the same reference numeral and the description thereof will be omitted since they have been described with reference to FIG. 2. The implantable medical device 20' may include activity level sensing means 41 for sensing an activity level of the patient connected to the controller 27. The controller 27 may be adapted to determine whether a sensed activity level is within a predetermined activity level range and to, if the sensed activity level is found to be within the range, initiate an optimization procedure comprising the steps of: selecting a first PV or AV interval; and gradually adjusting the first PV interval or AV interval until an energy value corresponding to the first heart sound resulting from at least one delivered pacing pulse in accordance with a latest PV or AV interval is within a predetermined energy value range.

In addition, the implantable medical device 20' may include heart rate sensor 43 for sensing a heart rate of the patient connected to the controller 27. The controller 27 may be adapted to determine whether a sensed heart rate is within a predetermined heart rate interval and to initiate an optimization procedure if the sensed heart rate is determined to be within the predetermined heart rate interval.

Furthermore, the implantable medical device 20' according to the present invention comprises a position detecting sensor 35 arranged to detect a body position of the patient. For example, the position sensor 35 can adapted to detect a predetermined specific body position. In a one embodiment of the present invention, the position detecting means is a back-position sensor arranged to sense when the patient is lying on his or her back (or on his or her face). The position detecting sensor 35 is connected to the controller 27.

As the skilled man realizes, only one, some of or all of the following features: the activity level sensing means 41, the heart rate sensor 43, a breathing rate sensor, the position detector 35, or the means for sensing signals related to the heart pumping activity of the patient may be included in the medical device according to the present invention.

Figure 4:
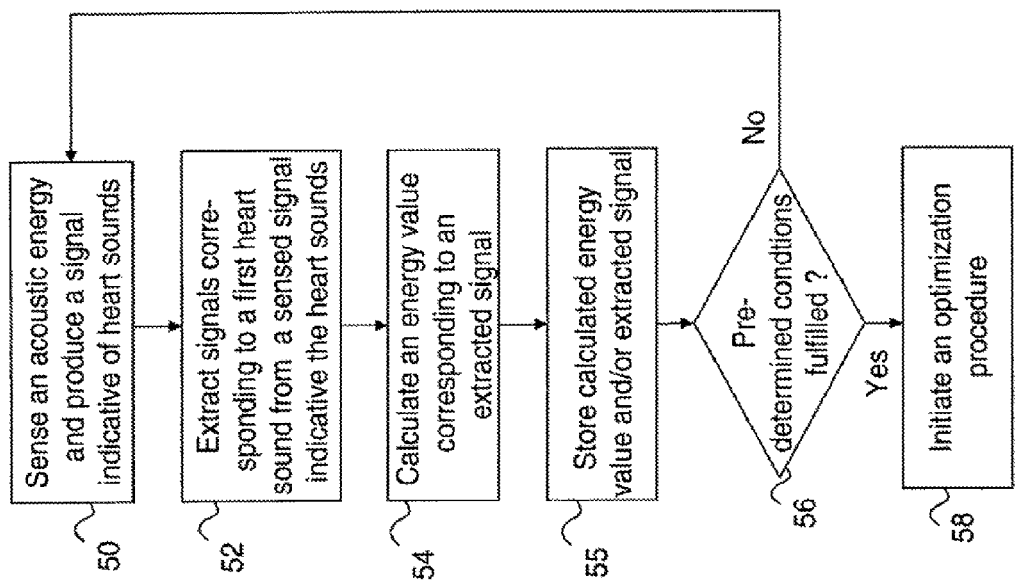
FIG. 4 is a flow chart of an embodiment of the method according to the present invention.
Figure 5:
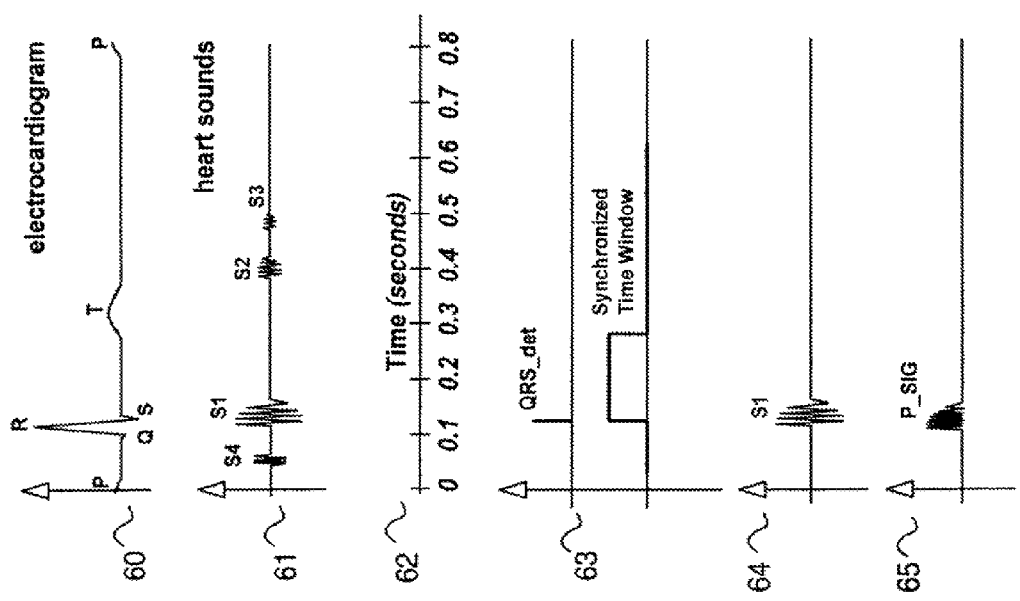
FIG. 5 shows a typical cardiac cycle, related heart sounds, and the resulting signals at a heart rate of 75 BPM.

Turning now to FIG. 4, a high-level description of the method according to the present invention will be given. First, at step 50, the acoustic sensor 29 senses an acoustic energy and produces signals indicative of heart sounds of the heart of the patient. In FIG. 5, a typical cardiac cycle, related heart sounds, and the resulting signals at a heart rate of 75 BPM are shown. A surface electrocardiogram and the related heart sounds S1, S2, S3, and S4 are indicated by 60 and 61, respectively, and a time axis is indicated by 62. In one embodiment, the acoustic sensor 29 is activated by the detection of a QRS-position, as indicated by 63, an intrinsic detected event or a paced event indicated by 60. The acoustic sensor 29 senses the acoustic energy in the heart sound S1, indicated by 61, during a sensing session having a predetermined length, for example, during a predetermined time window, indicated by 64. In this embodiment, the initiation of the sensing session is synchronized with the detection of the QRS-position, indicated by 63. The length of the time window is programmable and a typical length is about 200 ms. Hence, the acoustic sensor 29 receives a triggering signal from the controller 27 upon detection of the QRS-position by the input circuit 33. The produced signal corresponding to the first heart sound S1 is indicated by 65. This may be performed during successive cardiac cycles under control of the controller 27, which thus produces a time series of successive heart sound signals. The produced signal or signals indicative of the first heart sounds are supplied to the signal processing circuit 23 where, at step 52, a signal corresponding to a first heart sound (S1) is extracted from a sensed signal by the pre-processing circuits 30, 32. Optionally, this step may include performing a filtering procedure in order to filter the sensed signal. In one embodiment, frequency components of the signal outside a predetermined frequency range is filtered off and the absolute value of the sensed signal is calculated. The resulting signal is indicated by 66 in FIG. 5. In another embodiment, the first heart sound signal is determined to be a part of the sensed signal having an amplitude above a predetermined amplitude level.

Thereafter, at step 54, an energy value corresponding to the extracted signal, indicated by 66 in FIG. 5, corresponding to the first heart sound is calculated in the energy calculating circuit 34. Then, at step 55, the calculated energy values and/or the extracted signal may be stored in the memory means 31. If signals corresponding to the first heart sound is obtained for successive cardiac cycles, the signals and calculated energy values can be stored in the memory means 31 in consecutive time order. Subsequently, at step 58, an optimization procedure is initiated. Optionally, a check whether conditions, such as activity level of the patient or position of the patient, are suitable for performing an optimization procedure can be performed before the optimization procedure is initiated. That is, the optimization procedure is initiated only if certain predetermined conditions are fulfilled, for example, that a sensed activity level is within a predetermined activity level range. Thus, optionally, a optimization procedure condition check step 56 may be performed before the optimization procedure is initiated. If the predetermined condition (-s) is (are) fulfilled, the optimization step 58 is initiated. On the other hand, if the predetermined condition (-s) is (are) not fulfilled, the procedure returns to step 50.

Figure 6:
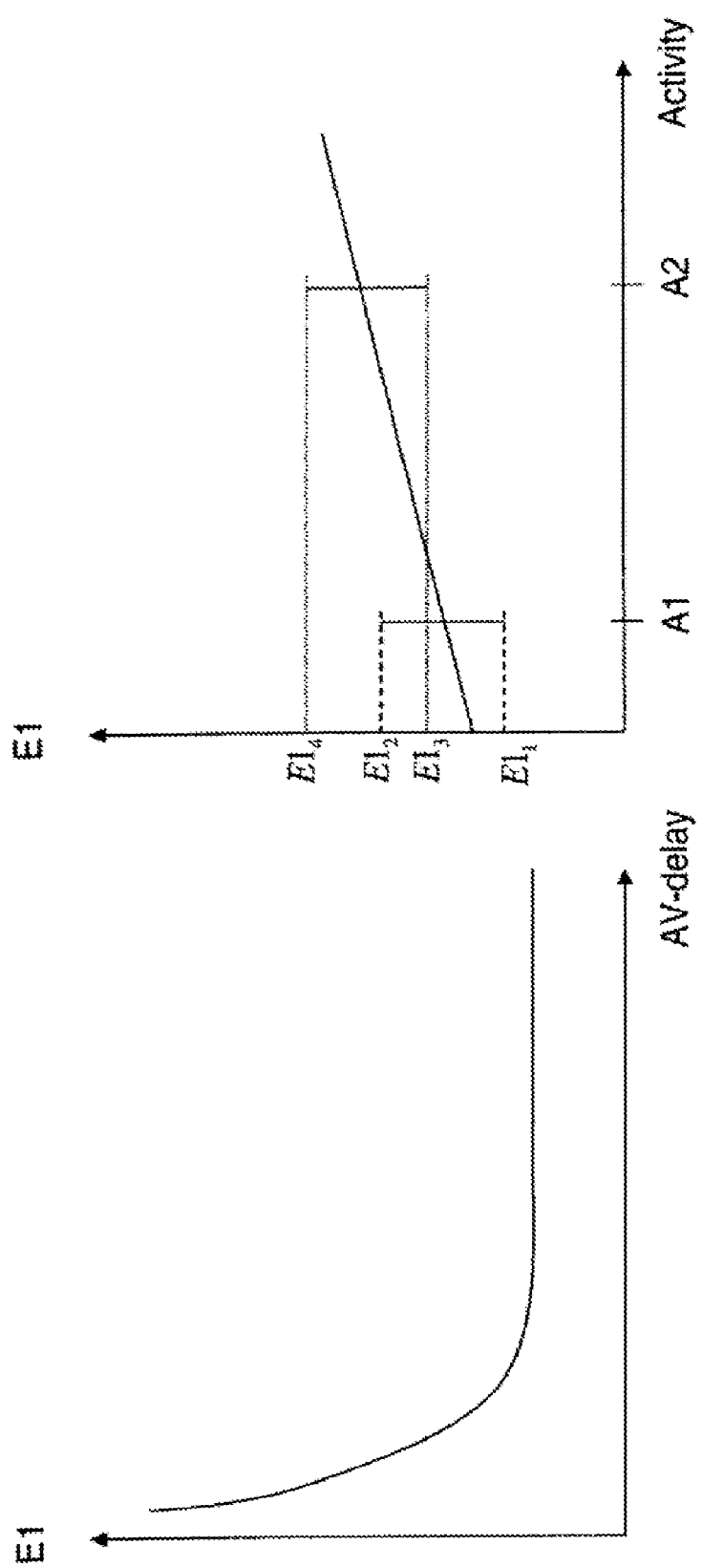
FIG. 6a is a diagram illustrating the relationship between the energy level corresponding to the first heart sound (S1) and AV-delay.
FIG. 6b is a diagram illustrating the relationship between the energy level corresponding to the first heart sound (S1) and activity level.
Figure 7:
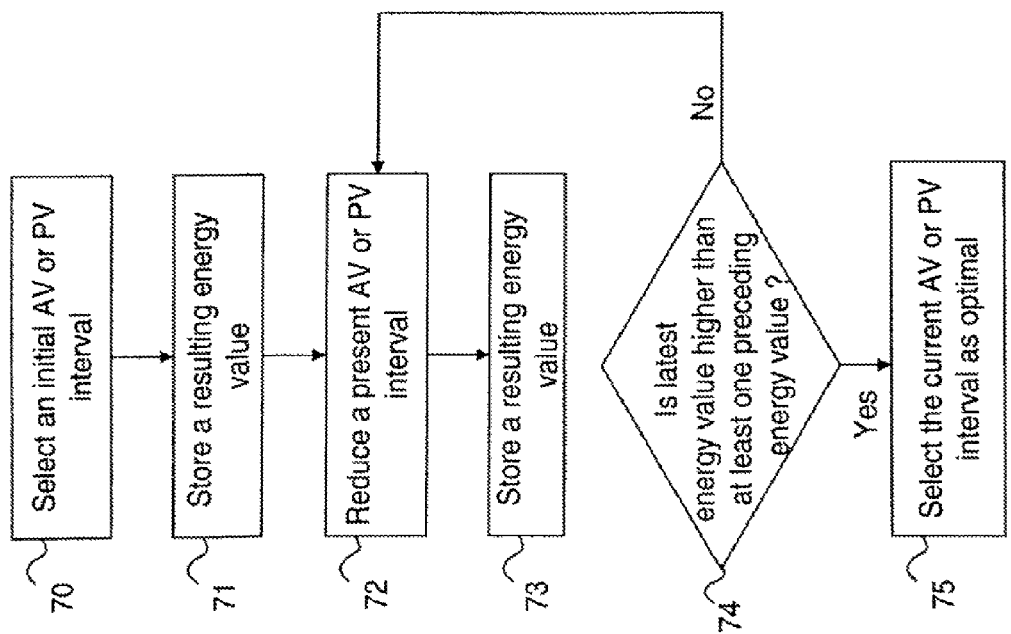
FIG. 7 is a flow chart of an embodiment of the optimization procedure according to the present invention.
Figure 8:
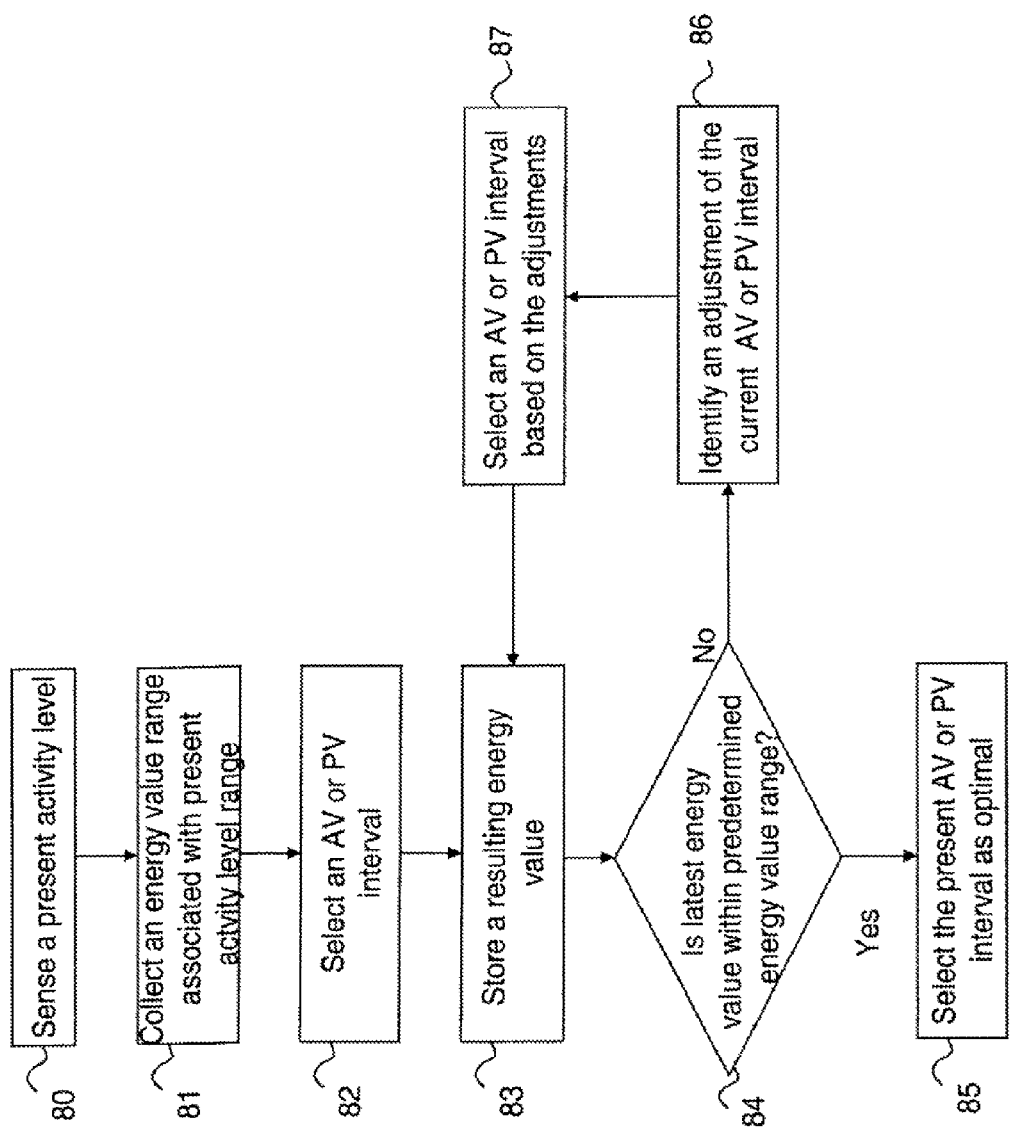
FIG. 8 is a flow chart of another embodiment of the optimization procedure according to the present invention.

With reference now to FIGS. 6-8, embodiments of the optimization procedure will be described.

Referring first to FIG. 7, an embodiment of the optimization procedure where the fact that the E1 signal, i.e. the energy value corresponding to the first heart sound (S1), depends highly on the AV or PV interval is utilized will be described. To be precise, a too short AV interval gives an abnormally high E1 value while a long AV interval gives a low E1 value, as illustrated in FIG. 6a. First, at step 70, upon initiation of the optimization procedure, a first or initial PV or AV interval is selected. This first interval or delay is preferably relatively long, which, as can be seen in FIG. 6a, entails that an energy value corresponding to a first heart sound (S1) resulting from a delivered stimulation therapy using the first interval will be low. Then, at step 71, the energy value corresponding to the first heart sound resulting from the delivered pacing pulse (-s) is stored, which energy value can be obtained in accordance with the procedure described above with reference to FIG. 4. Thereafter, at step 72, the initial AV or PV delay is reduced. The AV or PV delay can be reduced in accordance with predetermined steps, which may be programmable. In step 73, the resulting energy value is stored, which energy value can be obtained in accordance with the procedure described above with reference to FIG. 4. Subsequently, at step 74, the latest energy value corresponding to the first heart sound resulting from the delivered pacing pulse (-s) in accordance with the latest PV or AV interval is compared with the energy value corresponding to the first heart sound resulting from delivered pacing pulse (-s) in accordance with the preceding PV or AV interval. If the latest energy value is determined to be higher than the preceding energy value with a predetermined factor, the procedure proceeds to step 75. If the latest energy value is lower than, equal to, or higher than, but with a factor being lower than the predetermined factor, the preceding energy value, the procedure returns to step 72 where the AV or PV delay is reduced again. In an embodiment, each energy value is compared with a mean value of a predetermined number of preceding energy values, for example, a weighted mean value. At step 75, the present AV or PV delay is identified to be the optimal delay or interval.

With reference now to FIG. 8, an embodiment of the optimization procedure where the fact that a certain amplitude of the E1 signal, i.e. the energy value corresponding to the first heart sound (S1), or a certain amplitude range is associated with a specific activity level or activity level range at a normal cardiac function. That is, at normal cardiac function there exists a suitable or optimal energy value or range for each activity level or activity level range, as illustrated in FIG. 6b. As can be seen, the activity level A1 is associated with an energy value range between $E1_1$, and $E1_2$ whereas the activity level A2 is associated with an energy value range between $E1_3$ and $E1_4$. First, at step 80, an activity level of the patient is sensed. Then, at step 81, an energy level range associated with the sensed activity level, or in fact a predetermined activity level range about the sensed activity level, is identified, i.e. the amplitude range associated with the sensed activity level or activity level range at a normal cardiac function. For example, the storage means 31 may contain a look-up table containing a list of energy level ranges each being associated with a specific activity level range and the controller 27 can be adapted to collect the energy value range corresponding to the activity level range comprising the sensed activity level. Subsequently, at step 82, an PV or AV interval is selected. Then, at step 83, the energy value corresponding to the first heart sound resulting from the delivered pacing pulse (-s) is stored, which energy value can be obtained in accordance with the procedure described above with reference to FIG. 4. Subsequently, at step 84, the energy value corresponding to the first heart sound resulting from the delivered pacing pulse (-s) in accordance with the latest PV or AV interval is compared with the pre-stored energy value range. If the energy value is within the pre-stored energy level range, the procedure proceeds to step 85 where the present AV or PV delay is identified to be the optimal delay or interval for the sensed activity level (or activity level range about the sensed activity level). If the energy value is outside the pre-stored energy level range, the procedure proceeds to step 86 where an adjustment of the present AV or PV delay is calculated, i.e. whether the delay should be lengthened or shortened depending on whether the latest energy value is above or below the range, respectively. Then, at step 87, a new PV or AV interval is selected based on the adjustments calculated in step 86.

An ordered set of pre-set AV intervals and/or PV intervals may be programmed into the memory 31, for example, at the time of implant by the physician, and they can also be reprogrammed using a programmer via a programmer interface. This timing interval set may contain a range of AV intervals and/or PV intervals over which the controller 27 will automatically switch during an optimization procedure.

As described with reference to FIG. 3, an activity level of the patient can be sensed by means of the activity level sensor 41 and the controller 27 may be adapted to checked whether the sensed activity level is below a predetermined activity level. If it is determined the sensed activity level is below the predetermined activity level or activity level range, the optimization procedure is initiated as discussed with reference to FIG. 4. By performing the optimization at stable conditions, e.g. correlating the optimization procedure with a predetermined activity level, the accuracy and reliability of the procedure can be further enhanced. This predetermined activity level can, for example, be set such that the optimization is performed at rest. That is, in this case an AV or PV delay that is optimal for situations when the patient is at rest can be obtained. The controller 27 according to an alternative embodiment be adapted to check whether the sensed activity level is below a predetermined first activity level (or within a first range) or within a second activity level range between a second activity level and a third activity level, wherein second activity level can be equal to or higher than the first activity level or equal to or higher than an upper limit of the first range. If the sensed activity level is determined to be below the predetermined first activity level, an optimization procedure is initiated to identify a first AV or PV interval for the first activity level, and if the sensed activity level is found to be within the activity level range, an optimization procedure is initiated to identify a second AV interval or PV interval for the activity level range. Thus, the optimization can be performed at two activity levels, and the AV or PV interval can be optimized, for example, at rest and at an elevated activity level (e.g. at exercise), respectively. By knowing the optimal AV or PV delay at two activity levels, it is possible to extrapolate the data to obtain a rate adaptive AV or PV delay.

According to another embodiment, the body position of the patient is detected by means of the position sensor 35 and the controller 27 may be adapted to determine or check whether the patient is in at least one predetermined specific body position. If it is determined that the patient is in the predetermined position, an optimization procedure is initiated as discussed with reference to FIG. 4. By performing the optimization at stable conditions, e.g. correlating the optimization procedure with a predetermined position, the accuracy and reliability of the optimization procedure can be improved. Furthermore, the position sensor 35 may be adapted to detect two different positions of the patient and the controller 27 may be adapted to determine whether the patient is in one of this predetermined positions and initiate an optimization procedure when the patient is in one of them. Thereby, the optimization can be performed at two different positions, for example, when the patient is in supine (lying down) and when the patient is in an upright position and thus an optimal AV or PV delay can be obtained for the supine position and an optimal AV or PV delay can be obtained for the upright position. In this way, the AV or PV delay can be optimized during different conditions.

Although specific embodiments have been shown and described herein for purposes of illustration and exemplification, it is understood by those of ordinary skill in the art that the specific embodiments shown and described may be substituted for a wide variety of alternative and/or equivalent implementations without departing from the scope of the invention. Those of ordinary skill in the art will readily appreciate that the present invention could be implemented in a wide variety of embodiments, including hardware and software implementations, or combinations thereof. As an example, many of the functions described above may be obtained and carried out by suitable software comprised in a micro-chip or the like data carrier. This application is intended to cover any adaptations or variations of the preferred embodiments discussed herein.

We claim as our invention:

1. An implantable medical device comprising:
   a pulse generator configured to emit cardiac stimulating pacing pulses;
   a cardiac lead connected to said pulse generator and configured for placement relative to cardiac tissue of a patient to deliver said pacing pulses to said cardiac tissue;
   an acoustic energy sensor that senses acoustic energy in predetermined periods of a cardiac cycle during successive heart cycles of the patient, and that emits successive sensed signals respectively representing said acoustic energy in said predetermined periods during successive heart cycles;
   a signal processor supplied with said sensed signals and configured to extract an extracted signal representing the S1 heart sound from each of said successive sensed signals, and to calculate an energy value associated with each extracted signal representing the S1 heart sound;
   a storage unit; and
   a controller in communication with said signal processor and said storage unit and said pulse generator, and being configured to operate said pulse generator to control emission of said cardiac stimulating pacing pulses from said pulse generator, said controller being configured to, at selected times, initiate an optimization procedure to iteratively modify emission of said cardiac stimulating pacing pulses to optimize an interval selected from the group consisting of a PV interval and a AV interval with respect to said energy value, by setting said interval to a first interval length and iteratively reducing said first interval length and storing, in said storage unit, successively extracted signals representing the S1 heart sound and the respective energy values corresponding thereto, and successively comparing said stored successive energy values, and stopping reduction of said first interval length when a comparison between successive energy values indicates an increase in the energy value of the associated extracted signal representing the S1 heart sound, and operating said pulse generator, until a next optimization procedure, to cause said pulse generator to emit said cardiac stimulating pacing pulses with said first interval length that resulted in said increase, as an optimized length of said interval.

2. An implantable medical device as claimed in claim 1 wherein said controller is configured to gradually adjust said interval until said optimal interval with respect to said energy values can be determined.

3. An implantable medical device as claimed in claim 1 comprising:
   an activity level sensor that senses an activity level of the subject; and
   wherein said controller is configured, upon said initiation of said optimization procedure, to select a first interval and to iteratively adjust said first interval until an energy value corresponding to the first heart sound resulting from at least one delivered pacing pulse in accordance with at least one interval is within a predetermined energy value range associated with the sensed activity level.

4. An implantable medical device as claimed in claim 1 wherein said controller is configured to control delivery of ventricular pacing pulses to maintain a VV interval substantially constant during said optimization procedure, and to determine said interval selected from the group consisting of a PV interval and an AV interval to be optimal for said VV interval.

5. An implantable medical device as claimed in claim 4 wherein said controller is configured to iteratively adjust intraventricular pacing timing parameters for at least one electrode dependent on said energy values, and wherein said storage units stores said pacing timing parameters.

6. An implantable medical device as claimed in claim 1 wherein said signal processor comprises:
   a bandpass filter that filters out frequency components of said acoustic signal outside of a predetermined frequency range;
   a rectifier that rectifies the filtered signal to produce a signal containing only positive or zero values, or a squaring circuit that performs a squaring procedure on the filtered signal to produce a signal containing only positive or zero values; and
   wherein said signal processor further comprises an identifying unit that identifies at least one local maximum point coincident with a first heart sound signal, and an integrator that integrates said first sound signal in a predetermined time window containing said at least one local maximum point, to obtain an energy value corresponding to the first heart sound; or
   wherein said signal processor further comprises an amplitude threshold sensing unit that selects a part of said signal containing only positive or zero values above a predetermined threshold, and an integrator that integrates said part of said signal above said threshold, to obtain said energy value corresponding to the first heart sound.

7. An implantable medical device as claimed in claim 1, comprising:
   a position detector that detects a body position of the patient, and that emits a position signal dependent on the body position of the patient; and
   wherein said controller is supplied with said position signal and is configured to determine, from said position signal, whether said patient is in a predetermined body position, and to initiate said optimization procedure if said patient is in said predetermined body position to determine said optimal interval for that predetermined body position.

8. An implantable medical device as claimed in claim 1, comprising:
   an activity level sensor that detects an activity level of a patient and emits an activity level signal corresponding thereto; and
   wherein said controller is configured to determine whether said activity level sensed by said activity level sensor is below a predetermined activity level and, if the sensed activity level is below said predetermined activity level, to initiate said optimization procedure, or to determine whether said activity level is below a predetermined first activity level or within a predetermined activity level range between a second activity level and a third activity level; and wherein said controller is configured, if said sensed activity level is determined to be below said predetermined first activity level, to initiate said optimization procedure, and if said sensed activity level is determined to be within said activity level range, to initiate said optimization procedure.

9. An implantable medical device as claimed in claim 1, comprising a heart rate sensor that senses a heart rate of the patient and emits a heart rate signal representing the heart rate; and wherein said controller is configured to determine whether said heart rate is within a predetermined heart rate range, and if said heart rate is determined to be within said predetermined heart rate range, to initiate said optimization procedure.

10. An implantable medical device as claimed in claim 1 comprising a lead that carries said acoustic sensor, said lead being configured to locate said acoustic sensor at a location selected from the group consisting in the right ventricle of the heart, in the left ventricle of the heart, in a coronary vein of the heart, in the vena cava, epicardially, and in the thorax, or wherein said acoustic sensor is located in a housing of the device, or wherein said acoustic sensor is a sensor selected from the group consisting of accelerometers, pressure sensors and microphones.

11. A method for operating an implantable medical device to control a cardiac stimulation therapy, comprising the steps of:

from an implanted pulse generator emitting cardiac stimulating pacing pulses, and placing a cardiac lead connected to said pulse generator relative to cardiac tissue of a patient to deliver said pacing pulses to said cardiac tissue;

with an acoustic energy sensor, sensing acoustic energy in vivo in predetermined periods of a cardiac cycle during successive heart cycles of the patient, and emitting successive sensed signals respectively representing said acoustic energy in said predetermined periods during successive heart cycles;

in an implanted signal processor supplied with said sensed signals, extracting an extracted signal representing the S1 heart sound from each of said successive sensed signals, and calculating an energy value associated with each extracted signal representing the S1 heart sound; and from an implanted controller in communication with said signal processor and an implanted storage unit and said pulse generator, operating said pulse generator to control emission of said cardiac stimulating pacing pulses from said pulse generator by, in said controller at selected times, initiating an optimization procedure to iteratively modify emission of said cardiac stimulating pacing pulses to optimize an interval selected from the group consisting of a PV interval and a AV interval with respect to said energy value, by setting said interval to a first interval length and iteratively reducing said first interval length and storing, in said storage unit, successively extracted signals representing the S1 heart sound and the respective energy values corresponding thereto, and successively comparing said stored successive energy values, and stopping reduction of said first interval length when a comparison between successive energy values indicates an increase in the energy value of the associated extracted signal representing the S1 heart sound, and operating said pulse generator, until a next optimization procedure, to cause said pulse generator to emit said cardiac stimulating pacing pulses with said first interval length that resulted in said increase, as an optimized length of said interval.

12. A method as claimed in claim 11 comprising, in said optimization procedure, iteratively adjusting said interval until said optimal interval with respect to said energy values can be determined.

13. A method as claimed in claim 11 comprising the further steps of:

sensing an activity level of the patient;

determining whether the sensed activity level is within a predetermined activity level range;

if said sensed activity level is within said predetermined activity level range, initiating said optimization procedure; and in said optimization procedure, selecting a first interval, and iteratively adjusting said first interval until an energy value corresponding to the first heart sound resulting from at least one delivered pacing pulse in accordance with a latest interval is within a predetermined energy value range.

14. A method as claimed in claim 11 wherein said optimization procedure comprises:

controlling delivery of ventricular pacing pulses to maintain a VV interval substantially constant; and determining said interval selected from the group consisting of a PV interval and an AV interval to be optimal for said VV interval.

15. A method as claimed in claim 14 wherein said optimization procedure comprises:

iteratively adjusting interventricular pacing timing parameters for at least one electrode based on said energy values; and storing said pacing timing parameters.

16. A method as claimed in claim 11 comprising:

filtering out frequency components of said acoustic signal outside of a predetermined frequency range;

rectifying the filtered signal to produce a signal containing only positive or zero values, or squaring said filtered signal to produce a signal containing only positive or zero values; and identifying at least one local maximum point as being coincident with a first heart sound signal, and integrating the first heart sound signal in a predetermined time window containing said at least one local maximum point, to obtain an energy value corresponding to the first heart sound; or selecting a part of said signal containing only positive or zero values that is above a predetermined threshold, and integrating said part of said signal above said threshold, to obtain an energy value corresponding to the first heart sound.

17. A method as claimed in claim 11 comprising calculating the energy value by calculating each energy value as an average value over a predetermined number of successive energy values corresponding to successive first heart sound signals.

18. A method as claimed in claim 11 comprising:

detecting a body position of the patient;

determining whether the patient is in a predetermined body position; and initiating said optimization procedure if said patient is in said predetermined body position.

19. A method as claimed in claim 11 comprising:
sensing an activity level of the patient;
determining whether said activity level is below a predetermined activity level; and
if said activity level is below said predetermined activity level, initiating said optimization procedure; or
determining whether the activity level is below a predetermined first activity level or within an activity level range between a second activity level and a third activity level, and if said sensed activity level is below said predetermined first activity level, initiating said optimization procedure to determine an optimal interval for said activities below said first predetermined activity level, and if said sensed activity level is within said activity level range, initiating said optimization procedure to determine said optimal interval for said activity level range.

20. A method as claimed in claim 11, comprising:
sensing a heart rate of the patient;
determining whether the heart rate is within a predetermined heart rate range; and
if said heart rate is within said predetermined heart rate range, initiating said optimization procedure to determine an optimal interval for said heart rate range.

21. A method as claimed in claim 11 comprising locating said acoustic sensor on a lead at a location selected from the group consisting in the right ventricle of the heart of the patient, in the left ventricle of the heart, in a coronary vein of the heart, in the vena cava, epicardially, and in the thorax, or locating said acoustic sensor within a housing of the device, or employing an accelerometer, a pressure sensor or a microphone as said acoustic sensor.

22. A non-transitory computer readable storage medium encoded with programming instructions that operate a computerized implantable medical device comprising a pulse generator, a cardiac lead, an acoustic sensor, a signal processor, a storage unit, and a controller, said programming instructions causing said implantable medical device to:

emit cardiac stimulating pacing pulses from the pulse generator and, via the cardiac lead connected to said pulse generator delivering said pacing pulses to cardiac tissue;

operate the acoustic energy sensor to sense acoustic energy in predetermined periods of a cardiac cycle during successive heart cycles of the patient, said acoustic energy sensor then emitting successive sensed signals respectively representing said acoustic energy in said predetermined periods during successive heart cycles;

operate the signal processor to receive with said sensed signals and to extract an extracted signal representing the S1 heart sound from each of said successive sensed signals, and to calculate an energy value associated with each extracted signal representing the S1 heart sound; and cause the controller to operate said pulse generator to control emission of said cardiac stimulating pacing pulses from said pulse generator by, in said controller at selected times, initiating an optimization procedure to iteratively modify emission of said cardiac stimulating pacing pulses to optimize an interval selected from the group consisting of a PV interval and a AV interval with respect to said energy value, by setting said interval to a first interval length and iteratively reducing said first interval length and storing, in said storage unit, successively extracted signals representing the S1 heart sound and the respective energy values corresponding thereto, and successively comparing said stored successive energy values, and stopping reduction of said first interval length when a comparison between successive energy values indicates an increase in the energy value of the associated extracted signal representing the S1 heart sound, and operating said pulse generator, until a next optimization procedure, to cause said pulse generator to emit said cardiac stimulating pacing pulses with said first interval length that resulted in said increase, as an optimized length of said interval.

* * * * *